United States Patent [19]

Shimonaka

[11] 4,126,069

[45] Nov. 21, 1978

[54] MICROTOME

[75] Inventor: Tomoo Shimonaka, Hiratsuka, Japan

[73] Assignee: Kabushiki Kaisha Akashi Seisakusho, Japan

[21] Appl. No.: 823,160

[22] Filed: Aug. 9, 1977

[30] Foreign Application Priority Data

Dec. 13, 1976 [JP] Japan .............................. 51-149524

[51] Int. Cl.$^2$ ............................................... G01N 1/06
[52] U.S. Cl. ....................................... 83/703; 83/575; 83/605; 83/915.5
[58] Field of Search .................... 83/915.5, 577, 703, 83/575, 605, 414

[56] References Cited

U.S. PATENT DOCUMENTS

| | | | |
|---|---|---|---|
| 2,927,505 | 3/1960 | Haanstra | 83/915.5 X |
| 3,077,806 | 2/1963 | Hellstrom | 83/915.5 X |
| 3,205,747 | 9/1965 | Guth | 83/605 |
| 3,691,889 | 9/1972 | Forsstrom | 83/915.5 X |
| 3,771,405 | 11/1973 | Blum | 83/915.5 X |
| 3,828,641 | 8/1974 | Sitte | 83/915.5 X |

FOREIGN PATENT DOCUMENTS

| | | | |
|---|---|---|---|
| 624,598 | 9/1961 | Italy | 83/915.5 |
| 1,362,101 | 7/1974 | United Kingdom | 83/915.5 |
| 148,549 | 4/1962 | U.S.S.R. | 83/915.5 |

*Primary Examiner*—Frank T. Yost
*Attorney, Agent, or Firm*—Robert E. Burns; Emmanuel J. Lobato; Bruce L. Adams

[57] ABSTRACT

A microtome for stable production of continuously cut thin sections of a specimen for electronmicroscopic examination by an electromagnetic drive mechanism. Employing a lever hinged so as to swing in a dynamically balanced state, and a specimen holder attached to one end of the lever opposite to a knife, the electromagnetic mechanism drives the other end of the lever so that on every swinging of the lever the specimen is cut by the knife with accurate speed control for continuously cutting. Also, the electromagnetic drive realizes an automated specimen cutting cycle.

3 Claims, 4 Drawing Figures

MICROTOME

BACKGROUND OF THE INVENTION

This invention relates to a microtome for continuously cutting thin sections of specimens for electronmicroscopic examination. More particularly, it relates to a microtome employing electromagnetic means for the control of specimen cutting.

In a conventional microtome as illustrated in FIG. 1, a schematic front view of a conventional microtome, one end 4a of a lever 4 is fitted through a hinge 3 to a lever support 2 on a base 1. To the other end 4b of the lever 4 is attached a specimen holder 7 that holds a specimen 7a opposite to a knife 6 mounted on an inching stand 5. The specimen 7a is shown as being cut by moving up and down the lever 4 by means of a cord 9 having one end connected to a pulley 8 adapted to be reciprocatingly turned through a desired angle as indicated by the arrow, and having another end connected to lever 4 between hinge 3 and specimen holder 7.

In continuous cutting, the second and subsequent thin sections of the specimen 7a have been obtained by similarly operating the pulley 8 after sliding the inching stand 5 little toward the specimen 7a or thermally expanding the lever 4 by energizing an electric heater 10 wound therearound.

In such a known microtome, only the apparent cutting speed is controlled by externally regulating the motion of the lever 4 by its own weight. Therefore, it is difficult to accurately control the speed with which the specimen 7a is cut. Further, external vibrations add to the motion of the lever 4 because only one end thereof is cantilevered by the hinge 3. It has consequently been difficult to stably obtain continuously cut thin sections of the specimen 7a.

This invention is intended for solving the aforementioned problems. The object of this invention is to provide such a microtome as permits accurate control of the specimen cutting speed irrespective of its posture, stable production of continuously cut thin sections of specimen, and realization of an automated specimen cutting cycle, by use of electromagnetic means for the control of specimen cutting.

SUMMARY OF THE INVENTION

For achieving this object, the microtome of this invention features a table, a lever fitted to said table by a hinge so as to swing around a horizontal axis in a dynamically balanced state, relative to a knife. A specimen holder is attached to one end of said lever opposite said knife, and an electrically operated drive mechanism is provided at the opposite end of said lever to swing the lever so that a specimen held by said specimen holder is cut by said knife.

The microtome of this invention also features that said electrically operated drive mechanism comprises a fixed magnet and a moving coil fitted to said opposite end of the lever so as to lie in a space in said fixed magnet and that a compensating circuit is provided to erase resistance of said moving coil.

The microtome of this invention further features that said table is supported on a base with springs therebetween and that an electromagnetic attracting mechanism is interposed between said table and base, said mechanism being adapted to attract said table away from said knife against the force of said springs.

The microtome of this invention also features that an adjustable elastic spacer comprising a compression spring and an adjusting screw disposed in series therewith is interposed between said table and base to keep said table, which is returned by said springs on release of said electromagnetic attracting mechanism, in a position suited for cutting the specimen held in said specimen holder.

BRIEF DESCRIPTION OF THE DRAWINGS

Now a microtome embodied according to this invention will be described by reference to the accompanying drawings.

DESCRIPTION OF THE PREFERRED EMBODIMENT

Figure 1:
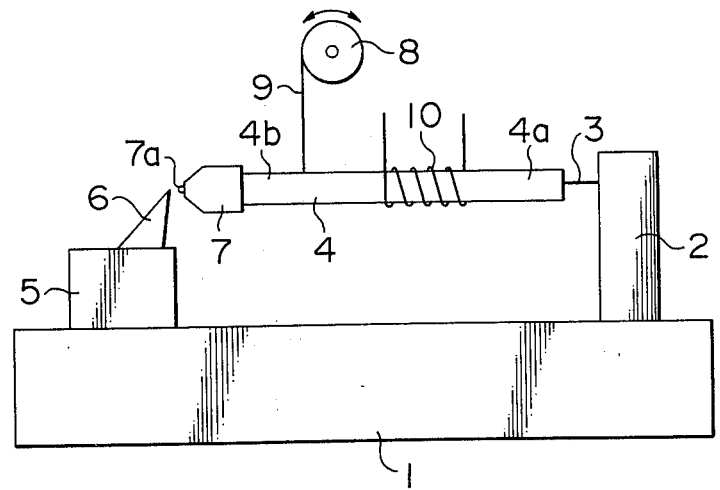
FIG. 1, as already described, shows a conventional microtome.
Figure 2:
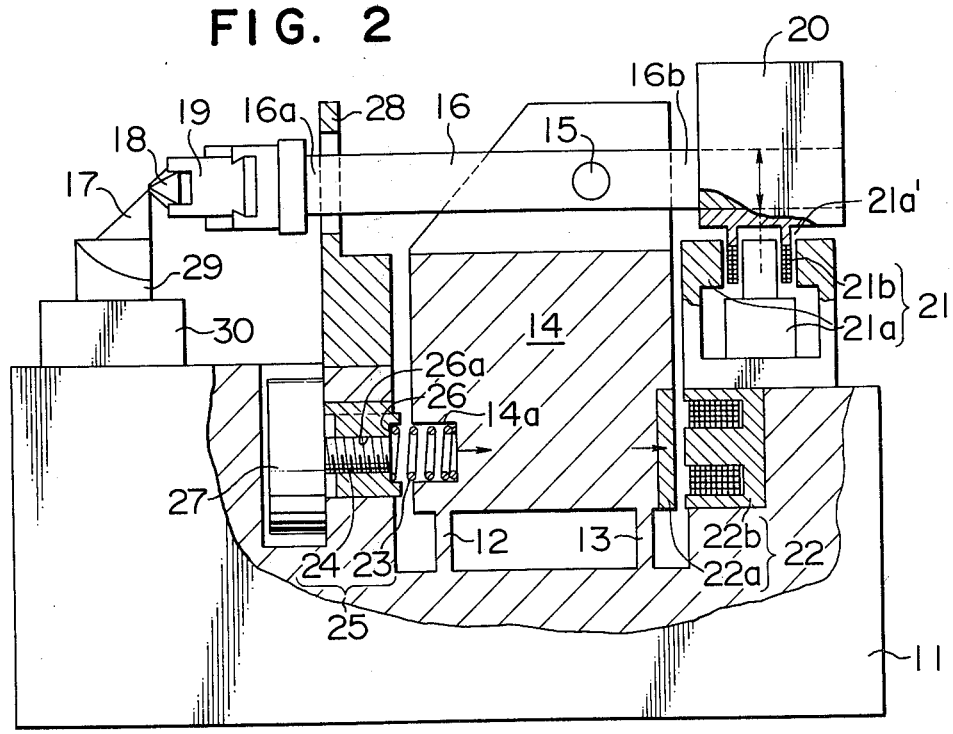
FIG. 2 is a front view of the new microtome, with a principal part thereof cut open.

In FIG. 2, a movable table 14 is placed on a base 11, with springs 12 and 13 interposed therebetween, so as to be slightly displaceable horizontally.

A lever 16 is fitted to the movable table 14 by a hinge disposed between two ends or the lever, and schematically shown at 15. The hinge may, for example, comprise cross spring arrangement (not shown). The lever is thereby swingable around a horizontal axis. A specimen holder 19 is attached to one end 16a of the lever 16 so that a specimen 18 is held opposite to a knife 17 in any direction or at any angle desired. An electrically operated drive mechanism 21 is fitted to the other and shortest end 16b of the lever 16 through a counterweight 20. This counterweight 20 permits the lever 16 to be swingably supported by the hinge 15 in a dynamically balanced state.

The electrically operated drive mechanism 21 comprises a fixed magnet 21a mounted on the base 11 and a moving coil 21b non-contactingly inserted in a space in the fixed magnet 21a. The fixed magnet 21a is shown as having an E-shaped cross-section and an annular coil space 21a' therein. The This moving coil 21b is fitted to the lower side of the opposite end 16b of the lever 16 through the counterweight 20.

An electromagnetic attracting mechanism 22, which attracts the movable table 14 away from the knife 17 against the force of the springs 12 and 13, is interposed between the movable table 14 and the base 11.

This electromagnetic attracting mechanism 22 comprises a magnetic member 22a attached to the movable table 14 and an electromagnet 22b attached to the base 11 opposite to said magnetic member 22a.

Further, an adjustable elastic spacer 25 comprising a compression spring 23 and an adjusting screw 24 disposed in series therewith is interposed between the movable table 14 and the base 11.

The adjusting screw 24 of the adjustable elastic spacer 25 is adapted to screw into an internal thread 26a formed at the approximate center of a spring shoe 26, and one end thereof is coupled to a motor 27 mounted on the base 11. The compression spring 23 of the adjustable elastic spacer 25 is inserted in a recess 14a in the movable table 14, with one end thereof being pressed by the spring shoe 26.

Accordingly, the spring shoe 26 is moved horizontally by turning the adjusting screw 24 to a desired extent by means of the motor 27. This changes the pressing force of the compression spring 23 against the movable table 14, thereby permitting a slight horizontal displacement of the movable table 14.

The control voltage is supplied to the moving coil 21b by circuit C as will be described, and to the electromagnet 22b and the motor 27 through respective lead wires not shown.

A frame 28, like a non-contacting pickup, is mounted on the base 11 so as not to contact but restrict the motion of the lever 16.

The frame 28 serves as a stopper to restrict the upper and lower limits of the motion of the lever 16 and detects the displacement of the lever 16 without contacting.

The knife 17 is fitted to an inching stand 30 through a knife holder 29 that permits adjustment of the specimen cutting angle. The inching stand 30 is mounted on the base 11 so that its relative position may be delicately adjusted.

The moving coil 21b may also be attached direct to the lower side of the opposite end 16b of the lever 16, not through the counterweight 20.

Figure 3:
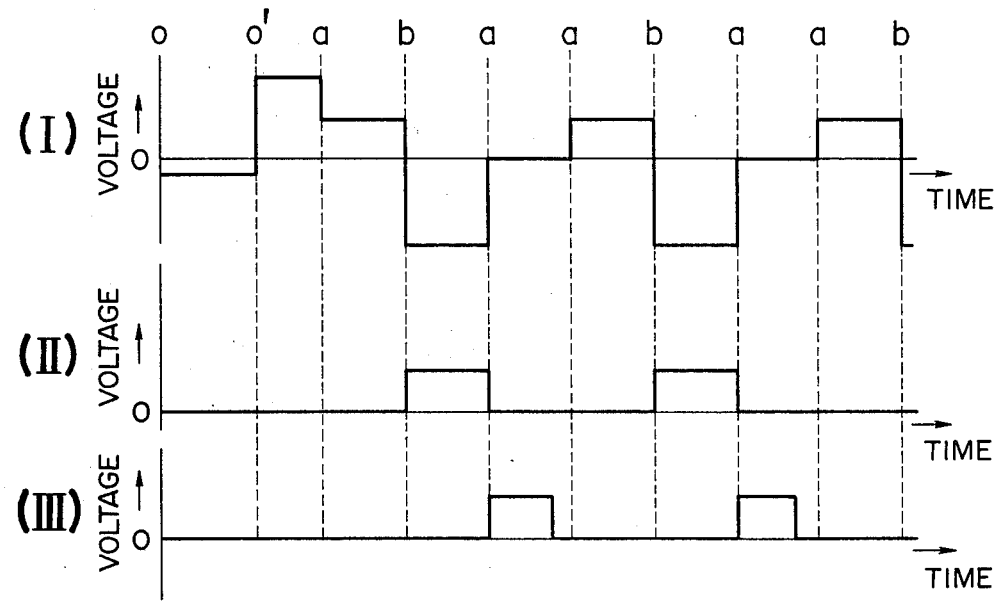
FIG. 3 is a timing chart of specimen cutting control, applied in the new microtome.

To continuously cut the specimen 18 into thin sections on the above-described microtome of this invention, a direct-current voltage is applied to the moving coil 21b as shown by o-o' on a timing chart (I) of FIG. 3. By thus pressing the lever 16 against the frame 28, the specimen 18 is put in the specimen holder 19. Then, the knife holder 29 and inching stand 30 are adjusted to set the knife 17 in a suitable position opposite to the specimen 18.

Next, a control voltage is applied to the moving coil 21b as indicated by o'-a in FIG. 3-(I). The frame 28, for detecting the lever position, detects when the specimen 18 has come to a position immediately before the knife 17 (indicated by point a in FIG. 3). By continuously applying a control voltage suited for the specimen 18 to the moving coil 21b in the range a-b in FIG. 3-(I), the knife 17 cuts the specimen 18 into a thin section that lies thereon.

That is, if a control voltage e is applied to the moving coil 21b, the moving coil 21b moves at a speed v, whereby the lever 16 is rotated and the specimen 18 is cut by the knife 17 and descends.

Let $e$ = the control voltage applied to the moving coil 21b, $i$ = the current passing through the moving coil 21b, $R$ = resistance of the moving coil 21b, $L$ = the length of the moving coil 21b, $v$ = the moving speed of the moving coil 21b and $B$ = the magnetic flux density developed in the fixed magnet 21a, then the following equation is obtained:

$$e = Ri + BLv \quad (1)$$

As it is possible to make $Ri << BLv$, the control voltage $e$ is expressed as follows:

$$e = BLv \quad (2)$$

Since the moving speed $v'$ of the specimen 18 is proportional to the leverage of the lever 16, the moving speed $v'$ can be controlled by the control voltage $e$ alone.

When the cutting of the specimen 18 has been completed (point b in FIG. 3-(I)), the polarity of the control voltage e applied to the moving coil 21b is reversed. In the range b-a of FIG. 3-(II), a voltage is applied to the electromagnet 22b to move the movable table 14 away from the knife 17.

As a consequence, the specimen 18 can be raised clear of the knife 17, thus freed from the risk of getting damaged.

When the specimen 18 lies immediately before the knife 17 (a-a in FIG. 3), a voltage is applied to the motor 27 to turn the adjusting screw 24 to a desired extent, as shown in FIG. 3-(III). This withdraws the spring shoe 26, whereby the pressing force of the compression spring 23 on the movable table 14 reduces and the balance between the forces of the springs 12 and 13 and the compression spring 23 is destroyed. Consequently, the movable table 14 is moved toward the knife 17 by a distance equal to the thickness of one thin section of the specimen 18, thereby establishing a new balanced state.

By repeating the above-described cycle as shown in FIG. 3, the specimen 18 can be continuously cut into a desired number of thin sections.

The control voltages e applied to the moving coil 21b, electromagnet 22b and motor 27 are controlled through relays or other known means by detecting the respective positions of the lever 16 by means of the frame 28. Otherwise, they may be process-controlled by programming their application procedures.

Figure 4:
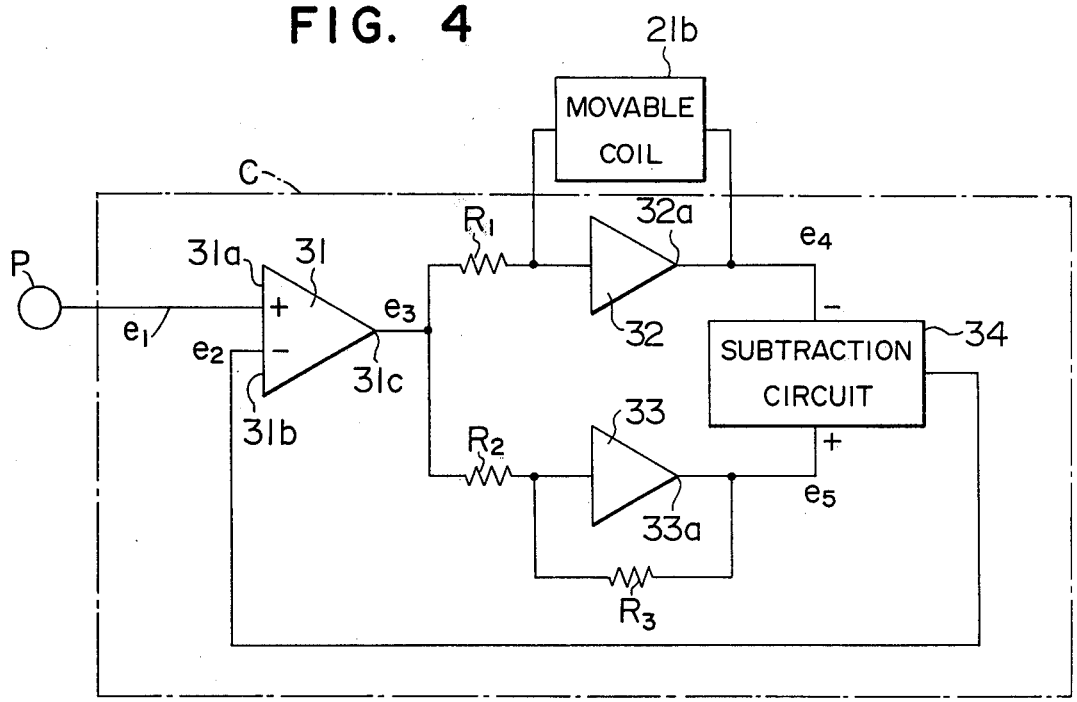
FIG. 4 shows a compensating circuit for the microtome which serves to eliminate resistance of a moving coil.

The term $Ri$ in the equation (1) can be substantially eliminated by a compensating circuit C shown in FIG. 4.

A differential amplifier 31 shown in FIG. 4 produces an output by amplifying the difference between two inputs A times. A plus input terminal 31a thereof is connected with a power supply P that feeds a control voltage $e_1$. An output terminal 31c connects with parallelized resistors $R_1$ and $R_2$.

The resistors $R_1$ and $R_2$ respectively connect with inversion amplifiers 32 and 33. The inversion amplifiers 32 and 33 in turn connect with the moving coil 21b and a resistor $R_3$, in parallel respectively.

Output terminals 32a and 33a of the inversion amplifiers 32 and 33 connect with a subtraction circuit 34, which in turn connects with a minus input terminal 31b of the differential amplifier 31.

An output voltage $e_3$ of the differential amplifier 31 in the circuit C of FIG. 4 is expressed:

$$e_3 = (e_1 - e_2)A \quad (3)$$

Assuming that the inversion amplifiers 32 and 33 amplify to sufficiently large extents, currents $i_1$ and $i_2$ passing through the resistors $R_1$ and $R_2$ become:

$$i_1 = e_3/R_1 \quad (4)$$

$$i_2 = e_3/R_2 \quad (5)$$

Then, output voltages $e_4$ and $e_5$ of the inversion amplifiers 32 and 33 are:

$$e_4 = -(Ri_1 + BLv) = -(e_3R/R_1 + BLv) \quad (6)$$

$$e_5 = -R_3i_2 = -e_3R_3/R_2 \quad (7)$$

By adusting to make $RR_2 = R_1R_3$, an output voltage $e_2$ of the subtraction circuit 34 becomes:

$$e_2 = e_5 - e_4 = BLv \quad (8)$$

From equations (3) and (8), $$e_1 = e_3/A + BLv \quad (9)$$

From equations (4) and (9), $$e_1 = R_1 i_1 / A + BLv \quad (10)$$

By making the resistance of the resistor $R_1$ equal to the resistance R of the moving coil $21b$, equation (10) becomes:

$$e_1 = R i_1 / A + BLv \quad (11)$$

Thus, the term Ri of equation (1) is reduced to $1/A$, and becomes negligible when A is large enough. Accordingly, the control voltage $e_1$ becomes as follows:

$$e_1 \approx BLv \quad (12)$$

Since the moving speed $v'$ of the specimen 18 is proportional to the leverage of the lever 16, the moving speed $v'$ can be controlled by the control voltage $e_1$ alone.

That is, the voltage drop of the moving coil $21b$, based on its resistance R is reduced and substantially eliminated by actuating the moving coil $21b$ by the differential voltage $e_3$ from the differential amplifier 31 and performing negative feedback of the voltage $e_2$ proportional to the moving speed $v$ of the moving coil $21b$ to the differential amplifier 31.

In the circuit of FIG. 4, the single moving coil $21b$ serves both for speed detection and for power generation. But it is also possible to divide the moving coil $21b$ into two independent coils so that one serves for speed detection and the other for power generation, with respective resistance compensating circuits to reduce the voltage drop of the moving coil $21b$ based on its resistance R.

The same circuit as described above that permits speed control by controlling only voltage can be composed even if the position of the speed detecting sensor on the lever 16 is changed. It is also possible to eliminate the resistance R of the moving coil $21b$ by feeding back output voltage to the differential amplifier 31 and making the resulting output impedance a negative resistance.

The microtome according to this invention is less susceptible to the influence of external vibrations since the lever 16 is kept in a dynamically balanced state by the counterweight 20 or other means. This insures the satisfactory cutting of the specimen 18 irrespective of the microtome posture.

As described above, the microtome of this invention employs the electrically operated drive mechanism that drives the lever with the specimen holder kept in a dynamically balanced state, the electromagnetic attracting mechanism and the adjustable elastic spacer as controlling means for permitting continuous cutting of thin specimen sections for electronmicroscopic examination. This microtome features simple structure, abilities for accurate specimen cutting speed control irrespective of posture and stable supply of continuously cut thin specimen sections uninfluenced by external vibrations.

Also, the microtome of this invention readily realizes the automation of the specimen cutting cycle since the electrically operated drive mechanism is used for specimen cutting control.

Moreover, in the microtome of this invention, operation as a microtome is performed reliably with very accurate specimen cutting. This is because the electrically operated drive mechanism comprises the fixed magnet and the moving coil interposed in the space thereof, and because the compensating circuit is provided between said moving coil and the power supply so as to reduce the voltage drop of the moving coil based on its resistance.

What is claimed is:

1. A microtome comprising:
   a table;
   a lever having a front end and an opposite end and fitted to the table so as to swing around a horizontal axis in a dynamically balanced state;
   a knife;
   a specimen holder attached to the first end of the lever opposite to the knife;
   an electrically operated drive mechanism, disposed at the opposite end of the lever, for effecting the swinging of the lever so that a specimen held by the specimen holder is cut by the knife, the drive mechanism comprising a fixed magnet having a coil space, and a coil fitted to and movable with the opposite end of the lever and disposed in the coil space of the fixed magnet; and
   a compensating circuit for energizing the coil, relative to the magnet, the circuit having a power supply, being interposed between the power supply and the coil, and being effective to reduce the voltage drop of the coil based on its resistance.

2. A microtome in accordance with claim 1, including a base; springs for supporting the table from the base; and an electromagnetic attracting mechanism, interposed between the table and base for attracting the table away from the knife against the force of the springs.

3. A microtome in accordance with claim 2, including an adjustable elastic spacer comprising a compression spring and an adjusting screw disposed in series therewith, interposed between the table and the base to keep the table in a position suited for cutting the specimen held in the specimen holder, subject to returning of the table by the spring on release of the electromagnetic attracting mechanism.

* * * * *